(12) United States Patent
Hwang et al.

(10) Patent No.: US 10,758,681 B2
(45) Date of Patent: Sep. 1, 2020

(54) SAFETY MODULE FOR INSERTION NEEDLE

(71) Applicant: Becton, Dickinson and Company, Franklin Lakes, NJ (US)

(72) Inventors: Charles Hwang, Wellesley, MA (US); Ralph Sonderegger, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 661 days.

(21) Appl. No.: 15/591,827

(22) Filed: May 10, 2017

(65) Prior Publication Data
US 2017/0326308 A1   Nov. 16, 2017

Related U.S. Application Data

(60) Provisional application No. 62/335,032, filed on May 11, 2016.

(51) Int. Cl.
*A61M 5/32* (2006.01)
*A61M 5/158* (2006.01)

(52) U.S. Cl.
CPC .......... *A61M 5/3204* (2013.01); *A61M 5/158* (2013.01); *A61M 5/3257* (2013.01); *A61M 2005/1585* (2013.01)

(58) Field of Classification Search
CPC .. A61M 5/3257; A61M 5/3204; A61M 5/158; A61M 2005/1585; A61M 2005/1586
See application file for complete search history.

(56) References Cited

U.S. PATENT DOCUMENTS

| 4,747,831 | A |   | 5/1988  | Kulli |
| 4,834,718 | A |   | 5/1989  | McDonald |
| 4,894,055 | A |   | 1/1990  | Sudnak |
| 4,944,725 | A |   | 7/1990  | McDonald |
| 5,501,675 | A | * | 3/1996  | Erskine ............ A61M 25/0631 604/263 |
| 5,562,631 | A |   | 10/1996 | Bogert |
| 5,575,777 | A |   | 11/1996 | Cover et al. |

(Continued)

FOREIGN PATENT DOCUMENTS

| EP | 2436311 A1 | 4/2012 |
| WO | WO-2013086439 A1 | 6/2013 |

*Primary Examiner* — Manuel A Mendez
*Assistant Examiner* — Tasnim Mehjabin Ahmed
(74) *Attorney, Agent, or Firm* — Dickinson Wright PLLC (57) ABSTRACT

A safety needle and hub module for selective connection with a medical device that includes a base and a head. The module includes a needle shield for selectively covering a distal end of a needle. A needle hub is movably received within a proximal opening of the needle shield, and extends through a passageway of the needle shield. An actuation button is movably received in opposing lateral apertures of the needle shield to engage the needle shield, the needle hub and the medical device. In a first position an upper leg of the actuation button is received in a recess of the needle hub, and a lower leg of the actuation button is received in an undercut between the base and head of the medical device. In a second position, after the actuation button is actuated, the module is removable from the medical device.

19 Claims, 9 Drawing Sheets

(56) References Cited

U.S. PATENT DOCUMENTS

| | | | |
|---|---|---|---|
| 5,713,876 | A | 2/1998 | Bogert et al. |
| 5,851,197 | A | 12/1998 | Marano et al. |
| 6,972,002 | B2 | 12/2005 | Thorne |
| 8,827,956 | B2 | 9/2014 | Banik et al. |
| 2004/0102740 | A1 | 5/2004 | Meloul |
| 2006/0173414 | A1 | 8/2006 | Buetikofer et al. |
| 2007/0276320 | A1* | 11/2007 | Wall .................... A61M 5/2033 604/68 |
| 2011/0118672 | A1 | 5/2011 | Hanson et al. |
| 2011/0178473 | A1* | 7/2011 | Richards ............. A61M 5/3257 604/198 |
| 2014/0058353 | A1 | 2/2014 | Politis et al. |
| 2014/0074033 | A1 | 3/2014 | Sonderegger et al. |
| 2019/0192772 | A1* | 6/2019 | Sonderegger ....... A61M 5/1626 |
| 2019/0224409 | A1* | 7/2019 | Sonderegger ........... A61M 5/32 |

* cited by examiner

SAFETY MODULE FOR INSERTION NEEDLE

RELATED APPLICATIONS

This application claims priority to U.S. Provisional Application Ser. No. 62/335,032, filed on May 11, 2016, which is hereby incorporated by reference in its entirety.

FIELD OF THE INVENTION

The present invention relates to safety modules, and more particularly, to a safety module with an insertion needle for protection against needle stick injury.

BACKGROUND OF THE INVENTION

Needle sharps safety is a growing and important aspect with regard to medical devices. Regulatory and market forces have both driven the need for a reliable means of protecting health-care professionals, custodial personnel and users from needle stick injury. The ability to protect users and personnel from needle stick injury is a critical aspect that influences the market success of a medical device.

The introduction of fluids into a patient using a catheter and insertion device is known. For intravenous infusion, a common insertion device is a syringe with an introducer needle received in a catheter. Currently there are several devices which prevent needle stick injury and enable the safe disposal of an introducer needle. These devices are often complicated, expensive and/or difficult to manufacture. Additionally, some previous devices have shown activation inconsistencies throughout their operating window.

As such, it may be appreciated that there is a continuing need for a new and improved safety module for an insertion needle that addresses the problems noted above and is simple and low-cost to manufacture. Embodiments of the present invention substantially fulfill this need.

SUMMARY OF EMBODIMENTS OF THE INVENTION

Accordingly, it is an aspect of the present invention to improved safety module for an insertion needle.

The foregoing and/or other aspects of the present invention are achieved by providing an apparatus, including: a safety needle and hub module for selective communication with a medical device including a base, the base having a column extending proximally from the base, and a head extending from the column, an undercut being formed by the column and the head. The safety needle and hub module has a needle shield for selectively shielding a distal end of a needle. The needle shield includes a circumferential wall with a proximal end and a distal end. The proximal end includes a proximal opening and the distal end includes a distal surface with a distal opening extending axially therethrough and communicating with the proximal opening to form an axial passageway. The outer wall has a pair of side posts connecting an upper wall portion with the distal end. The needle shield also includes a pair of transverse apertures disposed on opposing sides of the side posts and communicating with the axial passageway. A needle hub is movably received within the proximal opening and extends through the passageway of the needle shield. The needle hub has a proximal end, a distal end, and a sidewall extending therebetween. A needle is fixedly connected to the distal end of the needle hub. An actuation button is movably received in the transverse apertures of the needle shield to engage the needle shield, the needle hub and the medical device.

The foregoing and/or other aspects of the present invention are also achieved by providing an actuation button for use with a needle shield, a needle hub and a medical device. The actuation button includes an upper leg, a lower leg spaced apart from the upper leg, and a first wall joining the upper leg and lower leg at a first end. The first end includes a user actuation surface. The actuation button also includes a second wall, joining the upper leg and lower leg at a second end. In a first position, the actuation button is engaged with the needle hub and the medical device, thereby limiting movement among the needle shield, needle hub and medical device. In a second position, the safety needle and hub module are disengaged from the medical device, the safety needle and hub module are removable from the medical device and the actuation button remains engaged with the needle shield to prevent relative movement between the actuation button and the needle shield.

The foregoing and/or other aspects of the present invention are also achieved by providing a safety needle and hub module for selective connection with a medical device including a base, the base having a column extending proximally from the base and a head extending from the column forming an undercut between the base and the head. The safety needle and hub module includes a needle shield for selectively covering a distal end of a needle. The needle shield includes an outer wall with a passageway communicating with a proximal end and a distal end. The proximal end includes a proximal opening and the distal end includes a distal surface with a distal opening extending therethrough. Opposing apertures are disposed on the needle shield. A needle hub is movably received within the proximal opening and extends through the passageway of the needle shield. The needle hub has a proximal end, a distal end and a needle fixedly connected to the distal end of the needle hub. An actuation button is movably received in the opposing apertures of the needle shield to engage the needle shield, the needle hub and the medical device. The actuation button has an upper leg and a lower leg operably connected. In a first position, the upper leg of the actuation button is received in a recess of the needle hub, and the lower leg of the actuation button is received in the undercut between the base and head of the medical device. In a second position, after the actuation button is actuated, the needle shield and hub module are removable from the medical device.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Reference will now be made in detail to embodiments of the present invention, which are illustrated in the accompanying drawings, wherein like reference numerals refer to like elements throughout. The embodiments described herein exemplify, but do not limit the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

Figure 1:
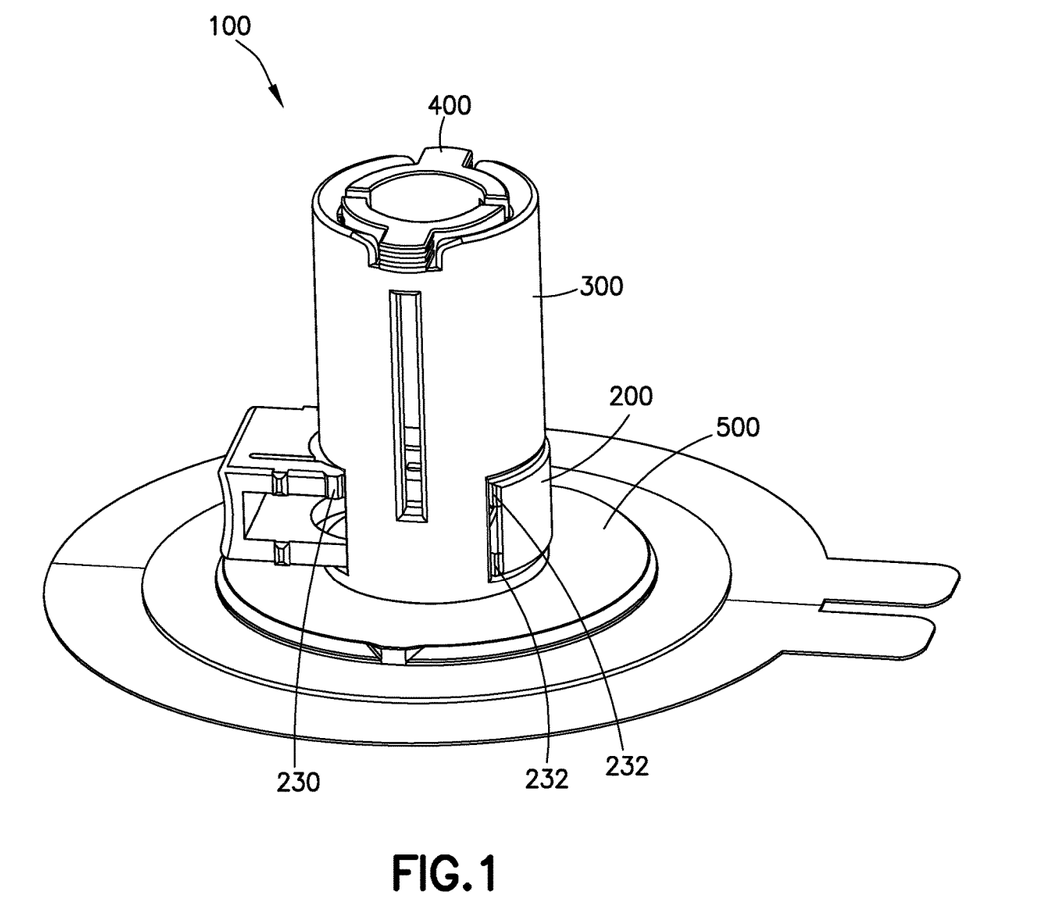
FIG. 1 is a perspective view of a safety module for an insertion needle, and an infusion set base in accordance with an embodiment of the present invention.
Figure 3:
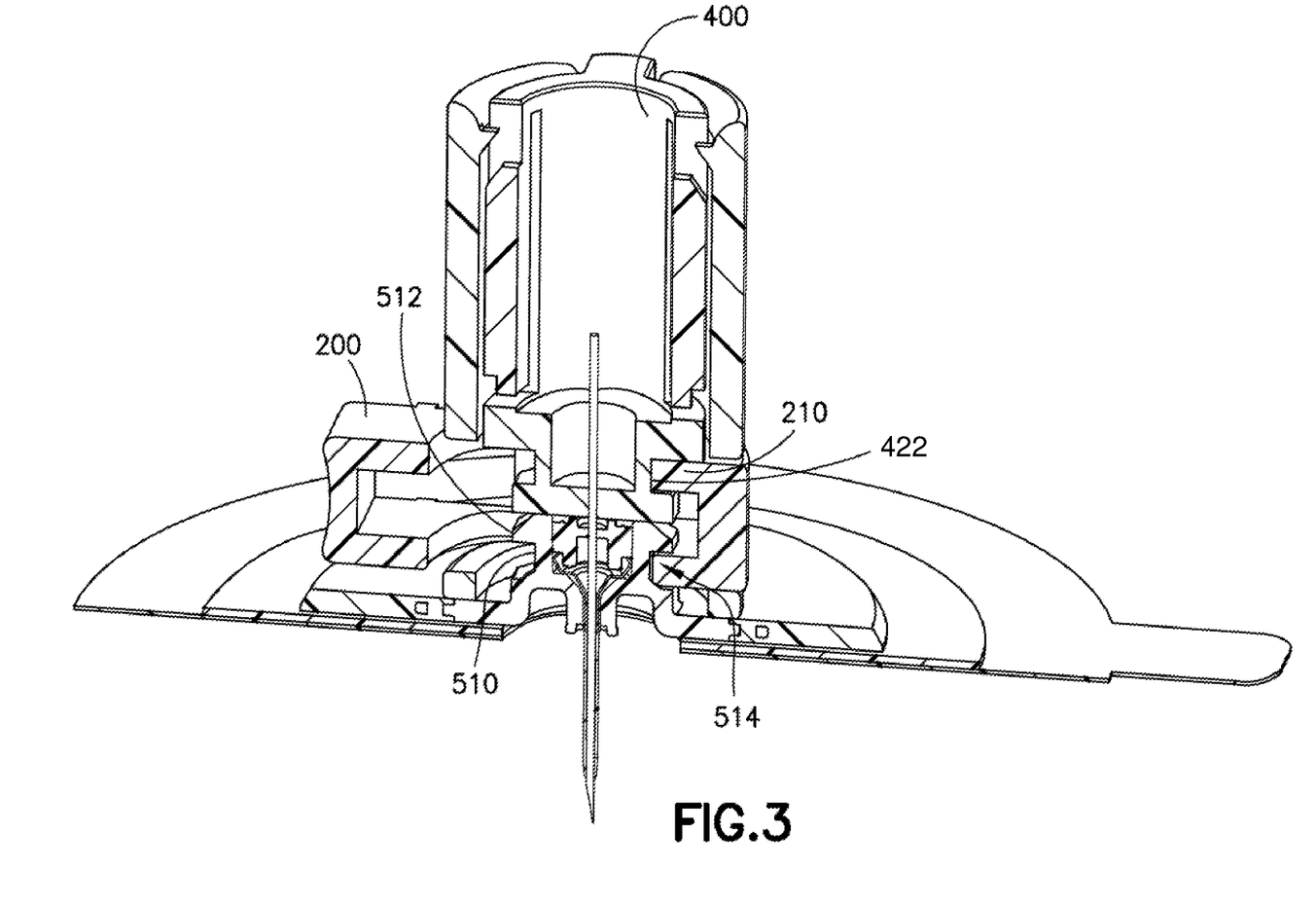
FIG. 3 is a cross-sectional view of the safety module of FIG. 1 in a first position.
Figure 6:
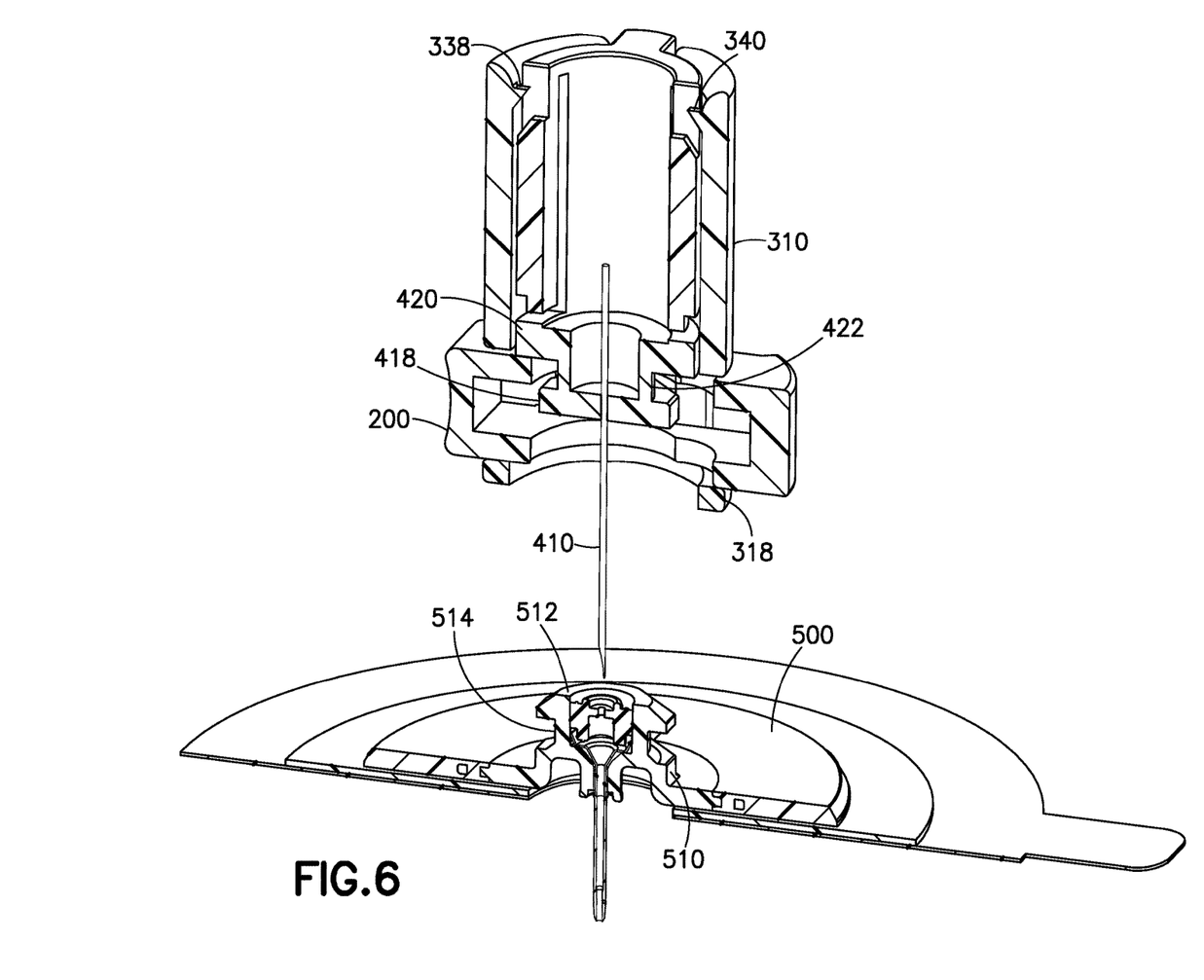
FIG. 6 is a cross-sectional view of the safety module of FIG. 1 but with the infusion set base omitted for clarity.

An infusion set base 500 and a safety module 100 are shown in FIG. 1. As best shown in FIGS. 3 and 6, the infusion set base 500 has a column 510 affixed thereto and a head 512 disposed on the column. An activation button 200 engages with a needle shield 300, a needle hub 400 and the base 500 via a transverse aperture 324 formed in needle shield 300 adjacent to the distal end of the needle shield 300. The activation button 200 includes a keyhole shaped opening 218, 234 that allows a needle 410 and the needle hub 400 to extend through the activation button 200.

Figure 2:
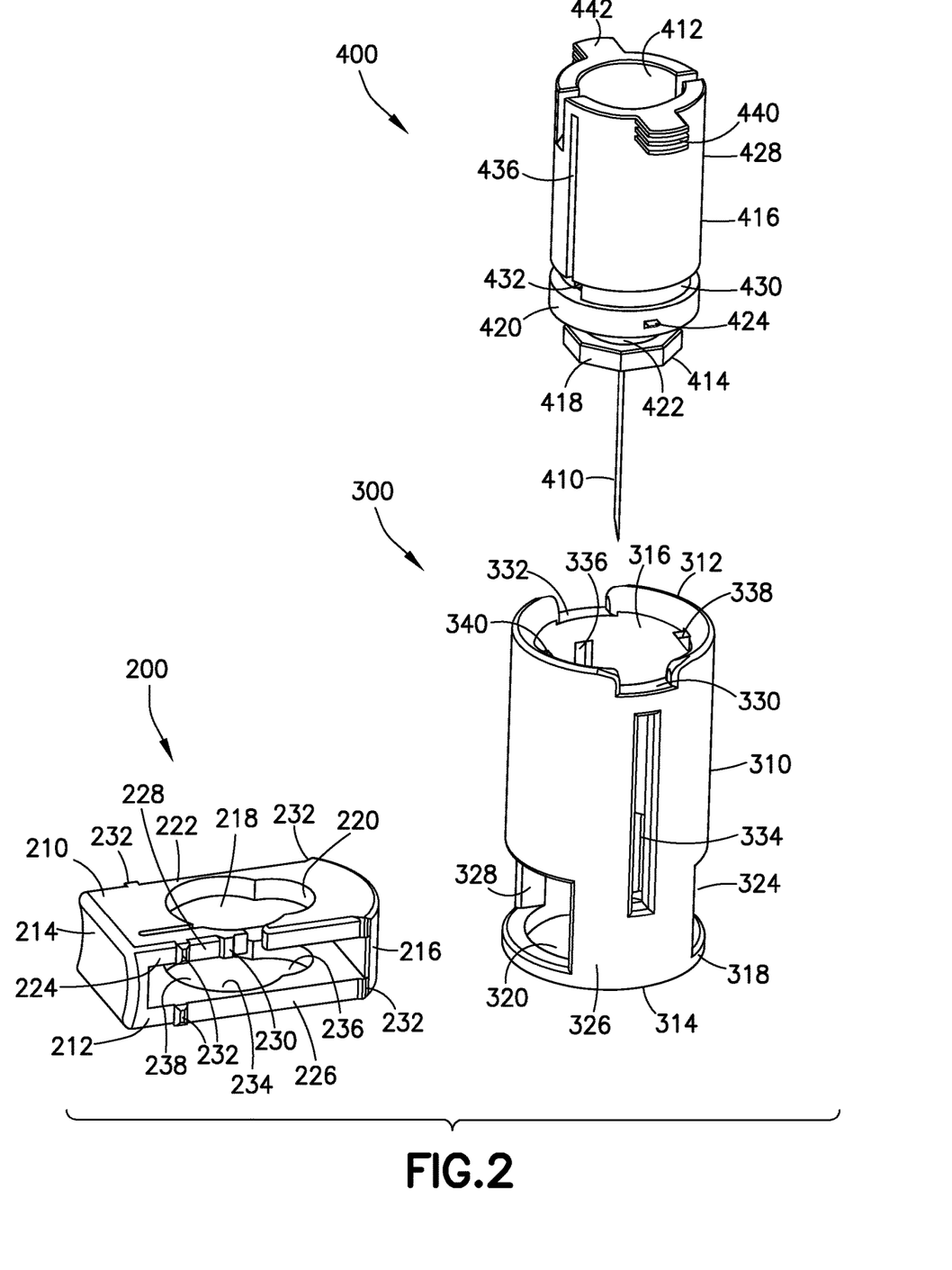
FIG. 2 is an exploded perspective view of the safety module of FIG. 1.

FIG. 2 is an exploded view of the safety module 100. As shown, the needle shield 300 for selectively covering a distal end of a needle 410 includes a circumferential wall 310 with a proximal end 312 and a distal end 314. The proximal end 312 includes a proximal opening 316 and the distal end includes a distal surface 318 with a distal opening 320 extending therethrough. A passageway 322 is formed by the wall 310 and extends between the proximal opening 316 and the distal opening 320. The transverse aperture 324 is formed in the wall 310 proximal to the distal surface 318. The transverse aperture 324 is formed between a first guide post 326 and an opposing second guide post 328 in the wall 310.

The first and second guide posts 326, 328 extend from the distal surface 320 towards the proximal end 312. A first cutout 330 and a second cutout 332 are formed on the wall 310 at the proximal end 312. According to one embodiment, the first cutout 330 and second cutout 332 are diametrically opposed to each other. Additionally, according to one embodiment, a first shield guide slot 334 and a second shield guide slot 336 are diametrically opposed from each other on the wall 310. According to one embodiment, the shield guide slots 334, 336 extend vertically (axially) from the first and second side posts 326, 328 to just below the first and second cutouts 330, 332 respectively. The first shield guide slot 334 and second shield guide slot 336 communicate with the transverse aperture 324 through the needle shield 300. A first shield protrusion 338 and a second shield protrusion 340 extend radially inwardly from an inner surface of the wall 310 at the proximal end 312.

The needle hub 400 can be movably received in the proximal opening 316 of the needle shield 300 and extend through the passageway 322 of the needle shield 300. The needle hub 400 includes a proximal end 412, a distal end 414, and a sidewall 416 extending therebetween. According to one embodiment, the needle 410 is fixedly connected to the distal end 414 of the needle hub 400. The needle hub sidewall 416 includes a flange 418 at the distal end 414. A collar 420 is proximal to and spaced away from the flange 418. A recessed notch 422 is formed by the space between the flange 418 and collar 420. The collar 420 includes opposed collar tabs 424, 426 to engage and move within the needle guide slots 334, 336 respectively. A tubular portion 428 is disposed proximal to and spaced away from the collar 420, and a recess 430 is formed by the space between the tubular portion 428 and collar 420.

The recess 430 includes opposed hub locking slots 432, 434 to lock the needle hub 400 relative to the needle shield 300 and prevent relative movement therebetween. A first hub guide slot 436 and a second hub guide slot 438 are axially, opposingly disposed on the tubular portion 428. The first and second hub guide slots 436, 438 extend from the hub locking slots 432, 434 to just below the proximal end of the needle hub. First and second gripping members 440, 442 are disposed at the proximal end 412 of the needle hub 400. The first and second gripping members 440 and 442 can be respectively received in the first 330 and second cutout 332 of the needle shield 300.

Figure 7:
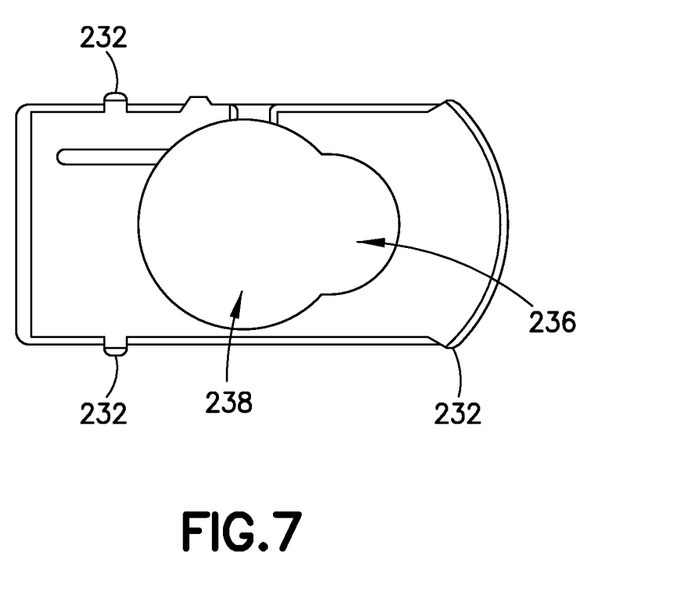
FIG. 7 is a top view of an actuation button on the safety module of FIG. 1.

The actuation button 200 includes an upper leg 210 and a lower leg 212 that are joined at a first end by a first wall 214 including a user actuation surface, and are joined at a second end by a second wall 216. The upper leg 210 and lower leg 212 extend laterally between the first 214 and second walls 216. The upper leg 210 includes a first hole 218 with a locking lobe 220 and an unlocking lobe 222. The locking lobe 220 is smaller than the unlocking lobe 222. The upper and lower legs 210 and 212 have respective first (upper) and second (lower) lateral faces 224 and 226. A cantilevered arm 228 with locking tab 230 is disposed on the first lateral face 224. A limiting tab is disposed 232 on the second lateral face 226. The lower leg 212 includes a second hole 234 with a locking lobe 236 and an unlocking lobe 238. The unlocking lobe 238 is larger than the locking lobe 236. The upper and lower legs 210 and 212 also have respective third (upper) and fourth (lower) lateral faces 240 and 242 disposed opposite to the first and second lateral faces 224 and 226. Preferably, limiting tabs 232 are also disposed on the third and fourth lateral faces 240 and 242.

As illustrated in FIG. 3, the infusion set base 500 can be removably engaged with the actuation button 200 via an undercut 514 formed by the column 510 and the overhang of the head 512. When the activation button 200 is in a first, or non-activated position, the upper leg 210 of the actuation button 200 is received in the flange recess 430 of the needle hub 400 and the lower leg 212 of the actuation button 200 is received in the undercut 514 formed by the column 510 of the infusion set base 500 and the head 512. Referring back to FIG. 1, the locking tab 230 and the limiting tab 232 of the upper leg 210 and the limiting tab 232 of the lower leg 212 engage the first guide post 326 of the needle shield 300 thereby locking the needle shield 300, needle hub 400 and head 512 together.

Figure 4:
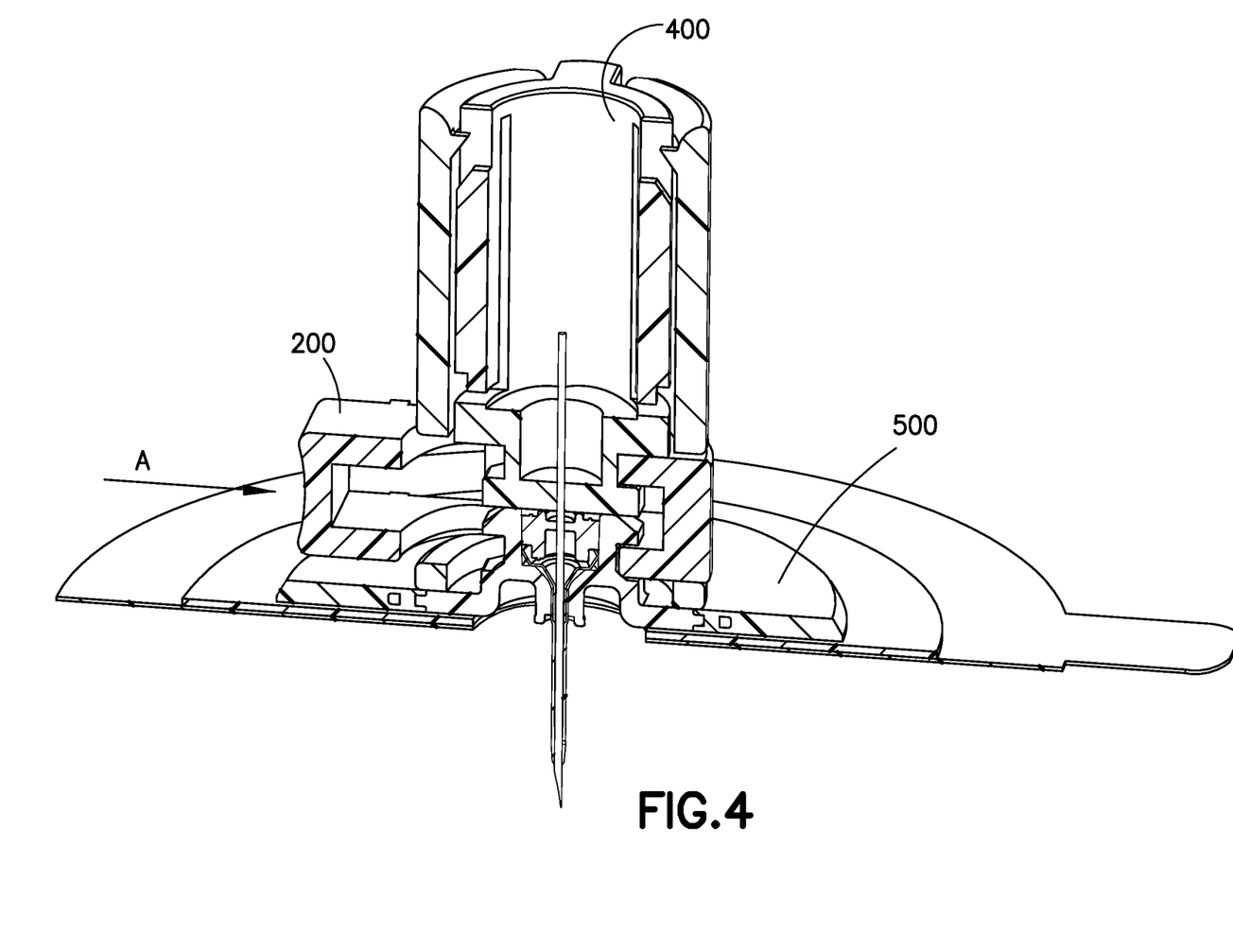
FIG. 4 is a cross-sectional view of the safety module of FIG. 1 in a second position.
Figure 5:
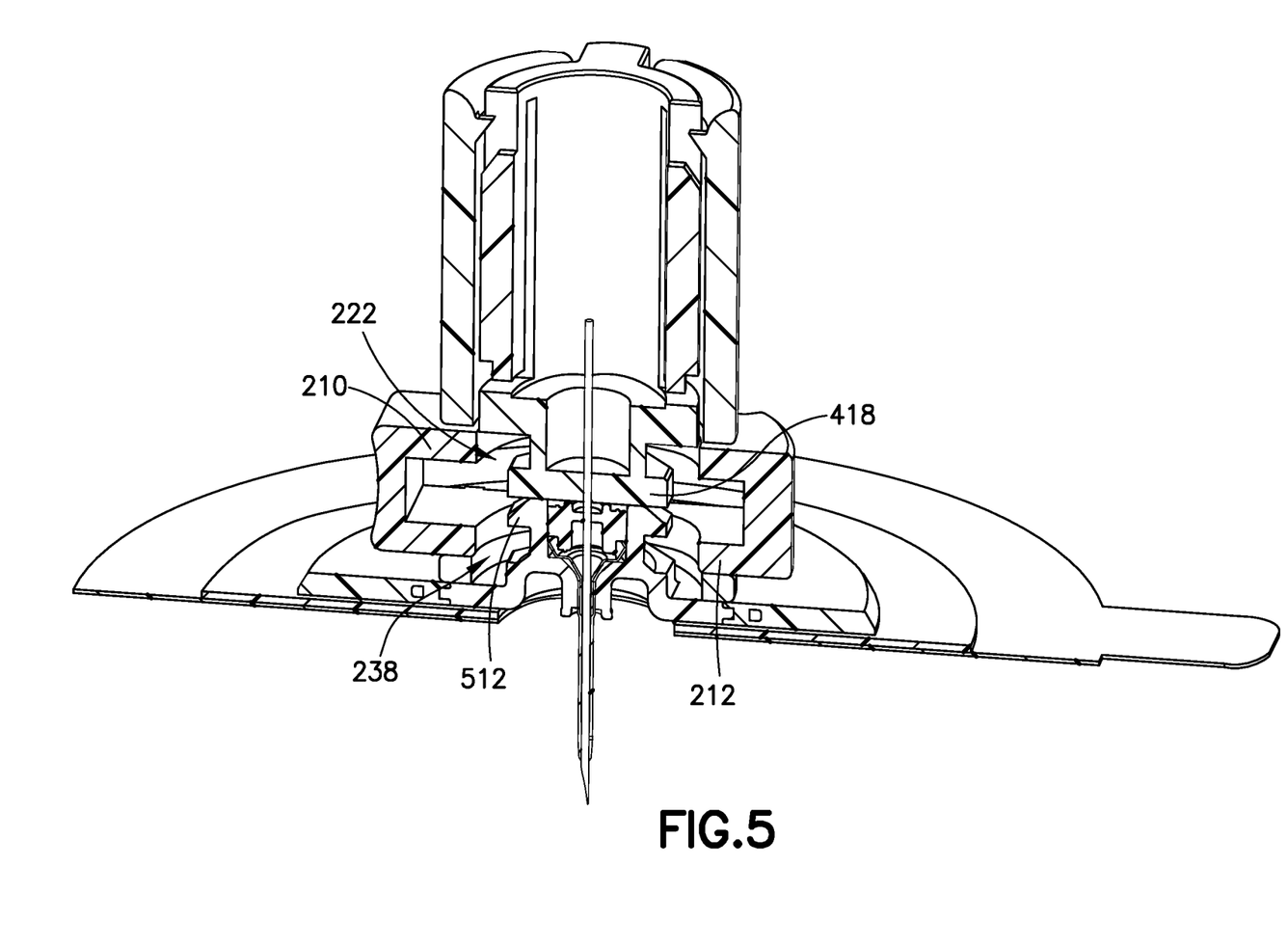
FIG. 5 is a cross-sectional view of the safety module of FIG. 1 in the second position.

FIG. 4 illustrates the direction that the activation button 200 is moved to unlock the base 500. Preferably, this direction is substantially perpendicular to the longitudinal axis of the needle hub 400. As shown in FIG. 5, in the second, or activated position, the infusion set head 512 is received in the unlocking lobe 238 of the lower leg 212 of the actuation button 200, and the flange 418 of the needle hub 400 is simultaneously received in the unlocking lobe 222 of the upper leg 210 of the actuation button 200. The respective unlocking lobes 222, 238 of the upper and lower legs are larger than the head 512 and the flange 418 on the needle hub 400. In the second position, the needle shield 300 and actuation button 200 may be removed from the head 512, as illustrated in FIG. 6.

Figure 8:
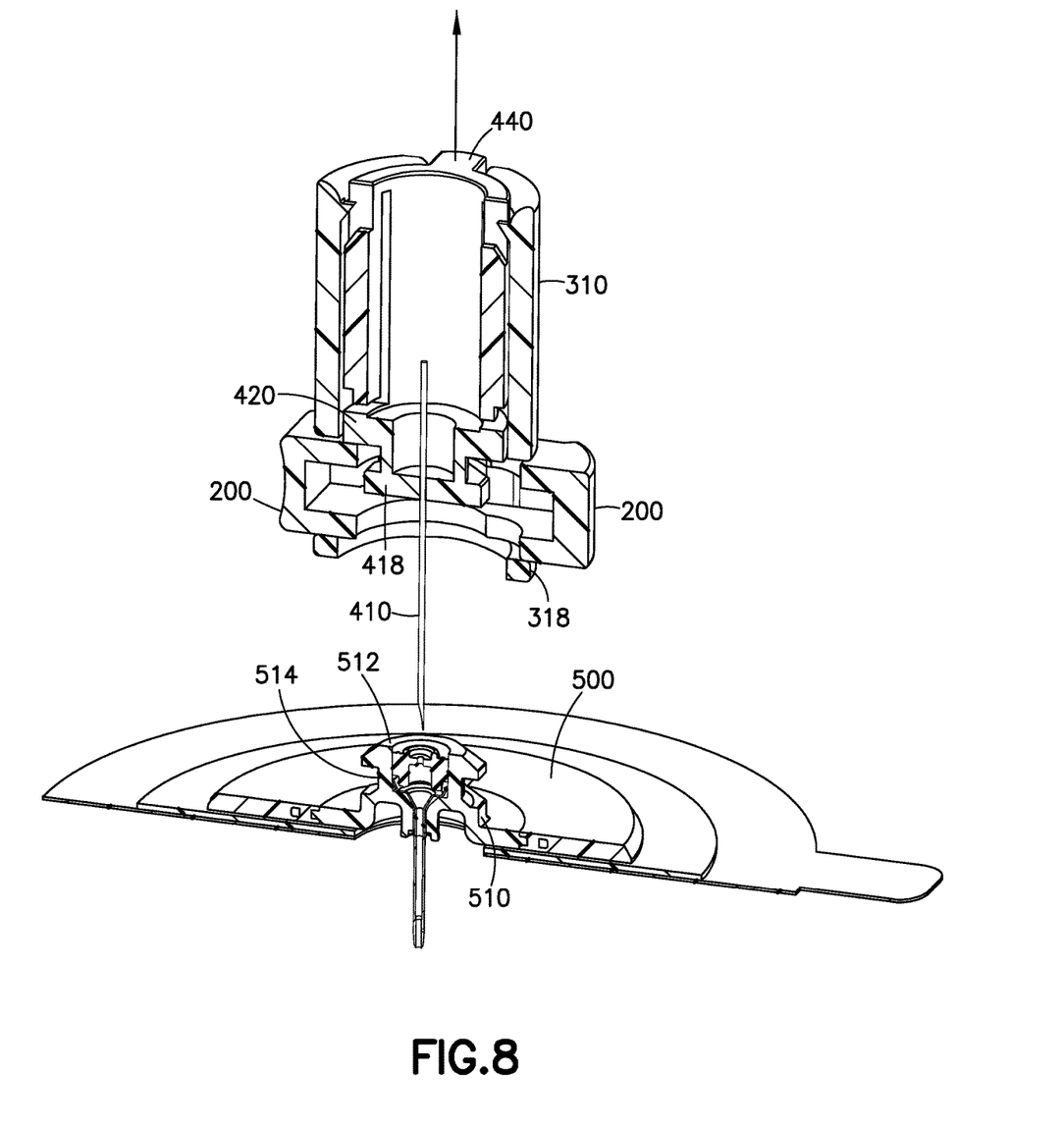
FIG. 8 is a cross-sectional view of the safety module of FIG. 1 with the needle hub in a locked position.
Figure 9:
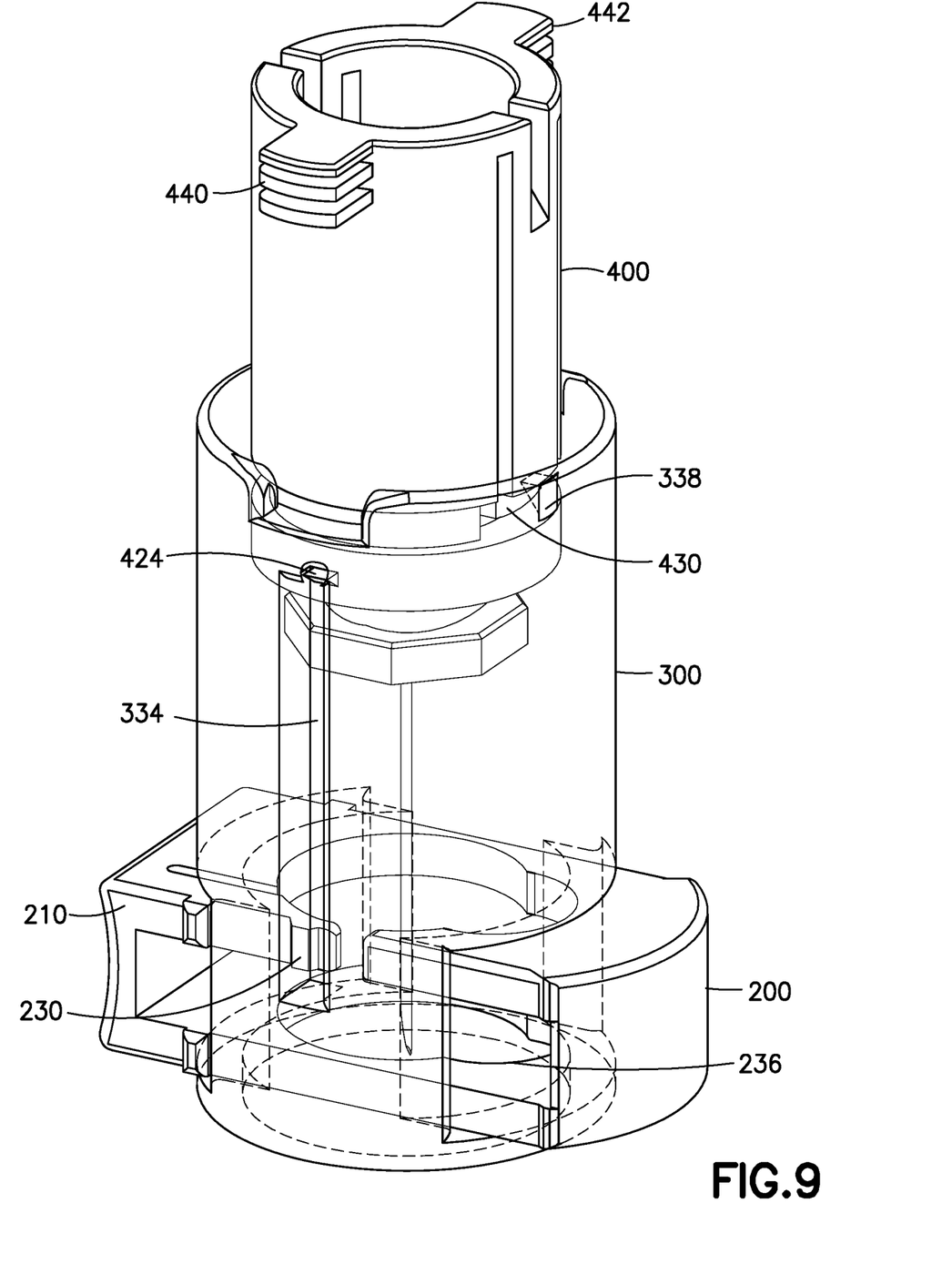
FIG. 9 is a perspective view of the safety module of FIG. 1 with the needle hub in a locked position with the infusion set base omitted for clarity.

FIG. 9 illustrates that in the second, activated position, the locking tab 230 of the upper leg 210 is received in the first shield guide slot 334 to prevent relative movement between the actuation button 200 and the needle shield 300. When the activation button is on the second, activated position, a user can move the needle hub 400 proximally relative to the needle shield 300 by engaging the gripping members 440, 442 and proximally sliding the needle hub 400 relative to the needle shield 300. The collar tabs 424, 426 on the needle hub 400 move proximally within the shield guide slots 334, 336 to withdraw the needle 410 into the shield 300. When the shield protrusions 338, 340 become seated in the collar recess 430 of the needle hub 400, the needle hub 400 becomes locked in the needle shield 300, and axial movement between the needle hub 400 and needle shield 300 is thereby prevented.

It will be appreciated by those skilled in the art that changes may be made to the embodiment without departing from the principles and spirit of the invention. Any of the embodiments and/or elements disclosed herein may be combined with one another to form various additional embodiments not specifically disclosed, as long as they do not contradict each other. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

What is claimed is:

1. A safety needle and hub module for selective connection with a medical device including a base, the base having a column extending proximally from the base, and a head extending from the column, an undercut being formed by the column and the head, the safety needle and hub module comprising:
    a needle shield for selectively shielding a distal end of a needle, including:
        a circumferential wall with a proximal end and a distal end, wherein the proximal end includes a proximal opening and the distal end includes a distal surface with a distal opening extending axially therethrough and communicating with the proximal opening to form an axial passageway, the circumferential wall having a pair of side posts connecting an upper wall portion with the distal end; and
        a pair of transverse apertures disposed on opposing sides of the side posts and communicating with the axial passageway;
    a needle hub movably received within the proximal opening and extending through the axial passageway of the needle shield, including:
        a proximal end, a distal end, and a sidewall extending therebetween; and
        the needle fixedly connected to the distal end of the needle hub; and
    a button having a pair of keyhole shaped openings and being movably received in the transverse apertures of the needle shield, wherein in a first position, a perimeter of one of the keyhole shaped openings interlocks with the needle hub and the perimeter of the remaining keyhole shaped opening interlocks with the medical device.

2. The safety needle and hub module of claim 1, wherein the actuation button comprises:
    an upper leg including a locking tab; and
    a lower leg, wherein the upper leg and lower leg are joined at a first end by a first wall including a user actuation surface, and joined at a second end by a second wall;
    wherein in the first position of the actuation button, the upper leg of the actuation button is engaged with the needle hub and the lower leg of the actuation button is engaged with the medical device to limit relative movement between the needle shield, needle hub and medical device, and
    in a second position of the button, after the actuation button is actuated, the lower leg of the actuation button is disengaged from the medical device, and the safety needle and hub module is removable from the medical device.

3. The safety needle and hub module of claim 2, wherein the needle shield further includes a first shield guide slot disposed on the circumferential wall extending proximally from one of the pair of side posts, wherein the first shield guide slot communicates with the transverse aperture; and
    the needle hub further includes a hub tab to engage and move within the first shield guide slot.

4. The safety needle and hub module of claim 3, wherein in the second position, the locking tab of the upper leg is received in the first shield guide slot to prevent relative movement between the actuation button and the needle shield.

5. The safety needle and hub module of claim 3, wherein the needle hub further comprises:
    a flange at the distal end of the sidewall; and
    a collar proximal to and spaced away from the flange;
    wherein the hub tab is disposed on the collar and a notch is formed between the flange and collar.

6. The safety needle and hub module of claim 5, wherein the upper arm of the actuation button is received in the notch of the needle hub in the first position.

7. The safety needle and hub module of claim 5, wherein the needle hub further comprises a tubular portion proximal to and spaced away from the collar, and a recess is formed between the tubular portion and collar.

8. The safety needle and hub module of claim 7, wherein the needle shield includes a first protrusion extending inwardly from an inner surface of the circumferential wall; and wherein the needle hub recess includes a first hub locking slot to lock the hub relative to the shield and prevent relative movement therebetween.

9. The safety needle and hub module of claim 2, wherein the upper leg of the actuation button further comprises:
opposing upper lateral faces;
wherein the locking tab is disposed on a cantilevered arm on one of the upper lateral faces, and a limiting tab is disposed on the remaining one of the upper lateral faces; and
wherein when the actuation button is in the first position, the locking tab and the limiting tab of the upper leg engage one of the side posts of the needle shield, thereby locking the actuation button, needle shield, needle hub, and head together.

10. The safety needle and hub module of claim 9, wherein the lower leg of the actuation button further comprises opposing lower lateral faces;
wherein a limiting tab is disposed on each of the lower lateral faces, and in the first position, one of the limiting tabs engages the one of the side posts of the needle shield thereby limiting movement between the actuation button, needle shield, needle hub, and medical device.

11. The safety needle and hub module of claim 10, wherein upper leg and the lower leg each have a hole with a locking lobe and an unlocking lobe, wherein the locking lobe is smaller than the unlocking lobe, and in the first position, the needle hub and medical device engage the locking lobe.

12. An actuatable button for use with a needle shield, a needle hub and a medical device, the button comprising:
an upper leg;
a lower leg spaced apart from the upper leg;
a first wall joining the upper leg and lower leg at a first end, wherein the first end includes a user actuation surface; and
a second wall, joining the upper leg and lower leg at a second end;
wherein in a first position the button is engaged with the needle hub and the medical device, thereby limiting movement among the needle shield, needle hub and medical device; and
in a second position the button is disengaged from the needle hub and the medical device, the needle shield and the needle hub are removable from the medical device, and the button remains engaged with the needle shield to prevent relative movement between the button and the needle shield.

13. The button of claim 12, wherein the upper leg and lower leg each include a hole with a locking lobe and an unlocking lobe, wherein the locking lobe is smaller than the unlocking lobe.

14. The button of claim 13, wherein in the first position, the needle hub is received in the locking lobe of the upper leg and the medical device is received in the locking lobe of the lower leg.

15. The button of claim 14, wherein the upper leg further comprises opposing upper lateral faces, wherein a cantilevered arm with locking tab is disposed on one of the upper lateral faces, and a limiting tab is disposed on the remaining one of the upper lateral faces.

16. The button of claim 15, wherein the lower leg further comprises opposing lower lateral faces, wherein a limiting tab is disposed on each of the lower lateral faces.

17. The button of claim 12, wherein the upper leg is substantially parallel to the lower leg.

18. A safety needle and hub module for selective connection with a medical device including a base, the base having a column extending proximally from the base, and a head extending from the column forming an undercut between the base and the head, the safety needle and hub module comprising:
a needle shield for selectively covering a distal end of a needle including:
an outer wall with a passageway communicating with a proximal end and a distal end, wherein the proximal end includes a proximal opening and the distal end includes a distal surface with a distal opening extending therethrough; and
opposing apertures disposed on the needle shield;
a needle hub movably received within the proximal opening and extending through the passageway of the needle shield, including:
a proximal end and a distal end; and
a needle fixedly connected to the distal end of the needle hub;
a button movably received in the opposing apertures of the needle shield to engage the needle shield, the needle hub and the medical device, wherein the button comprises:
an upper leg and a lower leg operably connected, wherein the upper leg and lower leg each include a hole with a locking lobe and an unlocking lobe;
wherein in a first position, the needle hub is received in the locking lobe of the upper leg and the medical device is received in the locking lobe of the lower leg.

19. The safety needle and hub module of claim 18, wherein in a second position, after the button is actuated, the safety needle and hub module is removable from the medical device.

* * * * *